United States Patent [19]
Urbanski

[11] Patent Number: 5,700,267
[45] Date of Patent: Dec. 23, 1997

[54] METHOD FOR REPAIRING BONE FRACTURES USING BONE-LOCK SYSTEM

[75] Inventor: Mark Gerald Urbanski, San Diego, Calif.

[73] Assignee: Kinetikos Medical Incorporated, San Diego, Calif.

[21] Appl. No.: 704,463

[22] Filed: Aug. 15, 1996

[51] Int. Cl.$^6$ ................................................ A61B 17/88
[52] U.S. Cl. ................... 606/86; 606/69; 606/72; 606/77; 606/96
[58] Field of Search ................... 606/53, 60, 72, 606/74, 75, 77, 86, 87, 69, 96; 623/16, 20; 144/144.1, 144.51, 354

[56] References Cited

U.S. PATENT DOCUMENTS

| | | | |
|---|---|---|---|
| 3,939,828 | 2/1976 | Mohr et al. | 606/72 |
| 4,655,203 | 4/1987 | Tormala et al. | 606/69 |
| 5,133,718 | 7/1992 | Mao | 606/69 |

OTHER PUBLICATIONS

Fred H. Albee, M.D., "Bone Graft Surgery in Disease,Injury and Deformity", 1940, pp. 30 and 212–215.

Primary Examiner—Michael Buiz
Assistant Examiner—David O. Reip
Attorney, Agent, or Firm—Baker, Maxham, Jester & Meador

[57] ABSTRACT

Bone fractures are stabilized by submerging a bone-lock mending key into the bone, avoiding detection of the key through the skin. A fractured bone typically includes two bone segments having complementary surfaces that mate at the fracture site. Bone repair begins by forming respective gripping channels in the two bone segments. The gripping channels are positioned such that, when the segments are mated at the fracture site, the channels form a continuous gripping socket that spans the fracture. The gripping socket is shaped to provide a longitudinal passage with multiple extensions proceeding outward from the passage. The extensions may comprise fingers, branches, and other apertures channeled outward from the longitudinal passage, thereby forming gripping features such as ridges, flanges, and other protuberances of bone. As an example, the gripping socket may form a "caterpillar" pattern, formed by multiple adjacent circular holes that are positioned in a line with a central passage extending through the circles. After forming the gripping socket, the bone segments are held together at the fracture site while a mending key is pressed into the socket. The mending key includes an elongated spar bearing multiple gripping protrusions shaped and sized to complementarily fit the socket's gripping features. Accordingly, when pressed into the socket, the socket's gripping features engage the key's gripping protrusions, thereby holding the mending key in place and stabilizing the bone segments.

28 Claims, 7 Drawing Sheets

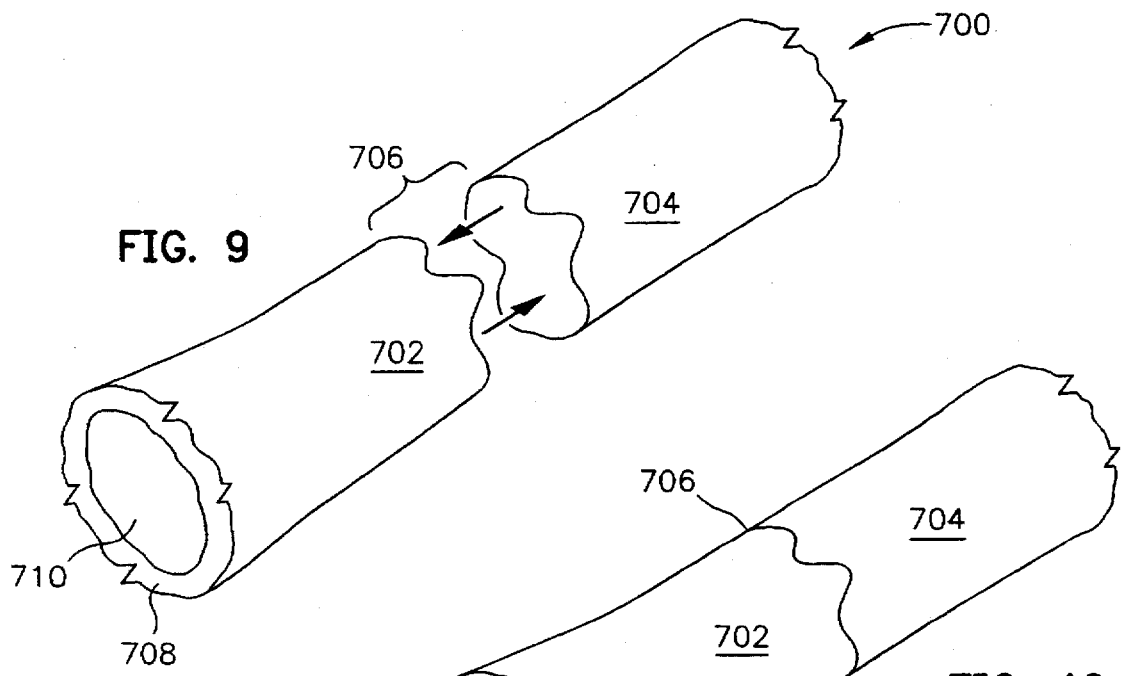
FIG. 9
FIG. 10
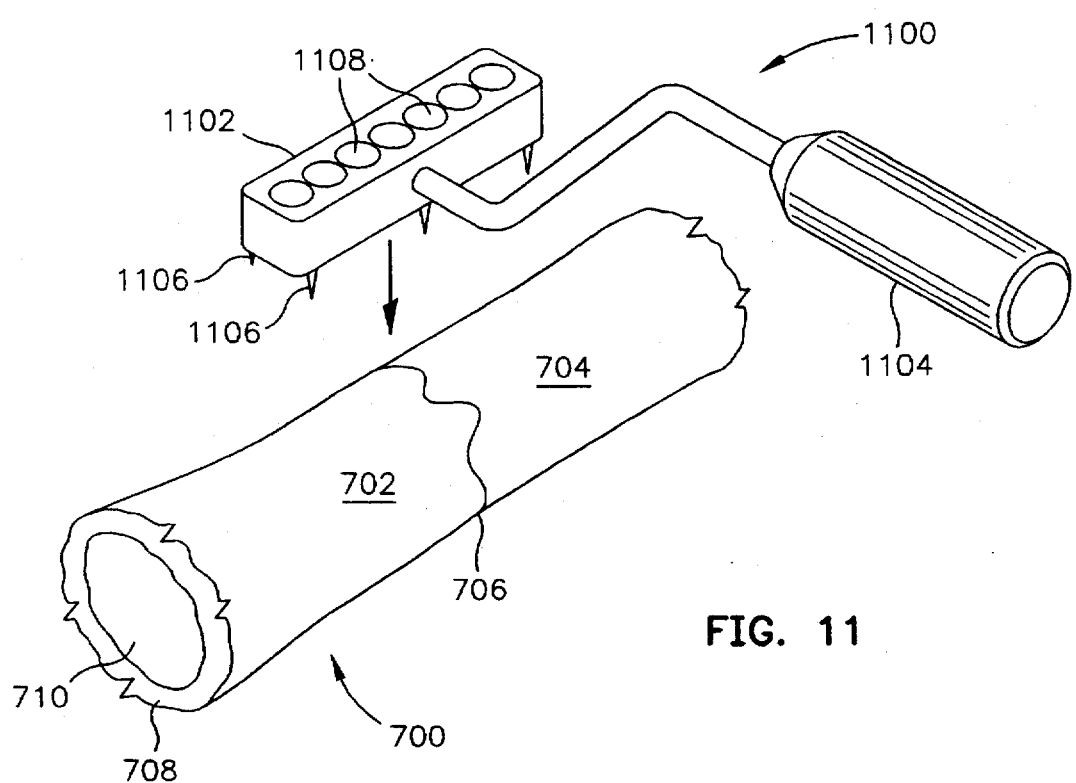
FIG. 11

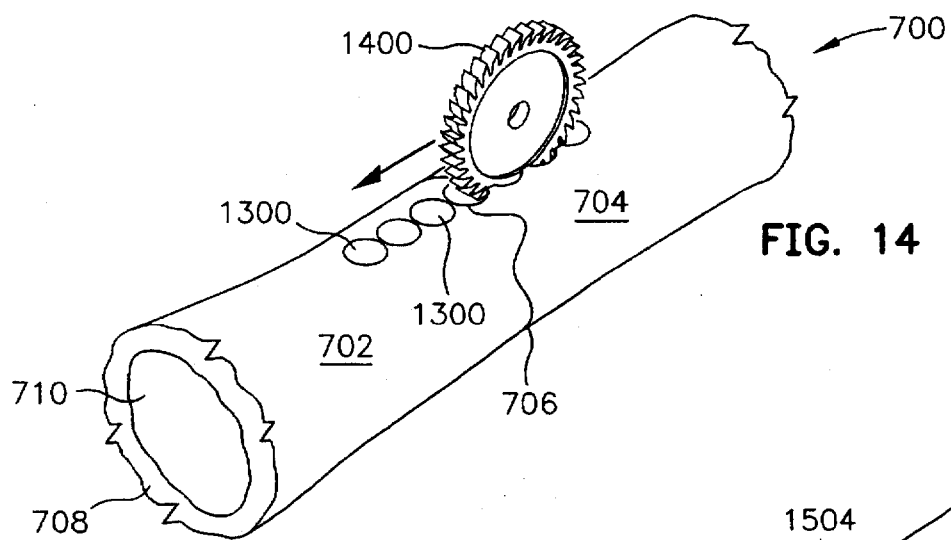
FIG. 14
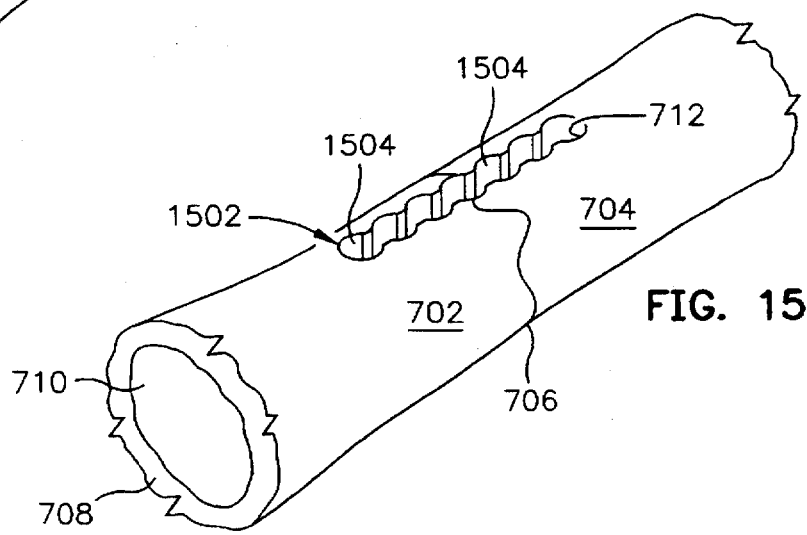
FIG. 15
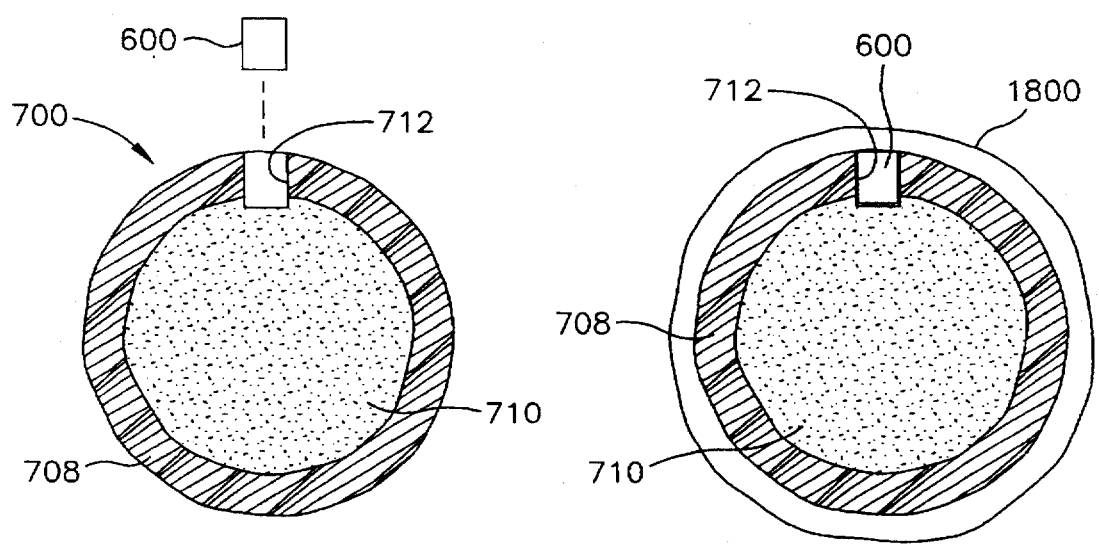
FIG. 16
FIG. 18

METHOD FOR REPAIRING BONE FRACTURES USING BONE-LOCK SYSTEM

BACKGROUND OF THE INVENTION

1. Field of the Invention

This invention generally concerns techniques for repairing bone fractures. More particularly, this invention involves a method for small bone stabilization using a "bone-lock" mending key that can be pressed or poured into the bone and submerged to avoid detection of the key through the skin. The key may be composed of a bio-absorbable material, which is later absorbed into the bone.

2. Description of Related Art

Many bone fractures today are repaired by first setting the bone with an immobilizing device and then waiting for the bone to mend back together. Some popular immobilizing devices include slings, rigid boots, splints, casts, and the like. Techniques such as these have worked well for decades, and these techniques continue to work well for many patients today.

For certain types of bone fractures, however, traditional techniques do not sufficiently immobilize the broken bone. Additionally, in some situations these techniques may be inadequate to firmly hold the bone parts together at the fracture site. To address these concerns, doctors have developed a extensive assortment of metal "overlay plates."

As shown in FIG. 1, an overlay plate 100 spans the segments 102–103 of a broken bone. Screws 106–107 attach the overplay plate 100 to the bone segments 102–103. Attached to the bone, the overlay plate 100 holds the bone segments together about the fracture site. Additional screws (not shown) may be used to prevent each bone segment from rotating with respect to the overlay plate. One example of the overlay plate 100 is made by the A.O. Synthes company of Switzerland.

FIGS. 2–4 depict further examples of overlay plates, including an Alphatec SFS Cloverleaf Plate (FIG. 2), an Alphatec SFS Small T Plate (FIG. 3), and an Ace Medical model 14330-12 (FIG. 4).

The known bone overlay plates can be useful in immobilizing bone fragments and holding them together, especially with large bones such as the femur and fibula. However, these devices are not properly suited for some applications. In particular, known bone overlay plates can be too bulky for repairing smaller bones such as the radius, tibia, ulna, and other extremity bones. FIG. 5 depicts a cross-sectional view of a small bone 500 with the overlay plate 100 installed. The plate 100 sits atop the cortical layer 502 of bone. The screw 106 protrudes through the plate 100 and cortical layer 502, and into the cancellous layer 504 of bone. The patient's dermis 506 or "skin" lies over the plate 100 and the cortical bone 502.

Due to the bulk of the plate 100 compared to the relatively small bone 500, the plate 100 may form an elevated area such as a visible "bump" or other enlarged area of the skin 506. In less severe cases, no elevated area is noticeable, but the patient may be able to detect the plate 100 through the skin 506 by touching the area with his/her fingers. Confronted with the possibility of having a permanent "bump" marking the fracture site, some patients might be reluctant to undergo this technique of bone repair. Furthermore, this construct (i.e., metal plates and screws) would remain in the patient permanently, and might present itself later as a stress point in the bone structure. Thus, the known bone repair techniques present certain potential drawbacks that may render them unacceptable for use in certain applications.

SUMMARY OF THE INVENTION

Broadly, this invention involves various techniques for repairing bone fractures by submerging a "bone-lock" mending key into the bone to avoid detection of the key through the skin. As an example, the invention is especially useful for stabilization of small bones such as the tibia, fibula, radius, ulna, or another one of the relatively smaller skeletal members.

The bone fracture defines first and second mating bone segments. The bone segments may have complementary surfaces that mate at a fracture site. In one embodiment, bone repair begins by forming respective gripping channels in the two bone segments. The gripping channels are positioned such that, when the segments are mated at the fracture site, the channels form a continuous gripping socket that spans the fracture. In this respect, it may be convenient to form the gripping channels while the bone segments are held together at the fracture site or "reduced," to provide a unitary structure replicating the bone as it existed prior to the fracture.

The gripping socket is shaped to provide a longitudinal passage with multiple gripping features extending outward from the passage. The gripping features may comprise fingers, branches, and other recesses carved in the bone to extend the longitudinal passage, thereby forming corresponding ridges, flanges, and other protuberances of bone. As an example, the gripping socket may form a "caterpillar" pattern, formed by multiple adjacent circular holes with a central longitudinal passage extending through the holes.

After forming the gripping socket, the bone segments are held together at the fracture site while the bone-lock mending key is placed into the socket. The mending key is preferably made of bio-absorbable material, which is ultimately absorbed and replaced by the patient's tissue during the healing process. The mending key may be formed from "hard" or "soft" materials. In the case of a hard mending key, the mending key includes a pre-shaped elongated member with multiple gripping protrusions configured to mate with the socket's gripping features. The hard mending key is pressed into the socket, whereupon the socket's gripping features engage the mending key's gripping protrusions, thereby holding the mending key in place. In addition, the hard mending key is snugly wedged into the gripping socket since the mending key is slightly larger than the gripping socket. In this respect, the hard mending key may be installed by using a pliers, vice, or another type of leverage.

As an alternative to the hard mending key, the soft mending key comprises a soft, plastic, fluid, or putty-like material that is poured, scooped, or injected into the socket and subsequently hardens in place. After hardening, the formerly soft mending key includes rigid gripping protrusions that engage the gripping features of the gripping socket.

After installation of a hard or soft mending key, the gripping protrusions of the mending key firmly engage the gripping features of the gripping socket, firmly holding the bone segments together. By securing the bone segments with the mending key, the fracture site is thus stabilized for proper rebuilding and healing of the bone.

BRIEF DESCRIPTION OF THE DRAWINGS

The nature, objects, and advantages of the invention will become more apparent to those skilled in the art after considering the following detailed description in connection with the accompanying drawings, in which like reference numerals designate like parts throughout, wherein:

FIG. 9 is an isometric diagram illustrating separated segments of a fractured bone, in accordance with the invention;

FIG. 10 is an isometric diagram illustrating abutting segments of a fractured bone, in accordance with the invention;

FIG. 11 is an isometric diagram illustrating the use of a template to mark a gripping socket in a fractured bone, in accordance with the invention;

FIG. 14 is an isometric diagram illustrating a cutting step during formation of the gripping socket of the invention;

FIG. 15 is an isometric diagram illustrating a completed gripping socket formed in accordance with the invention;

FIG. 16 is a side cross-sectional diagram showing the insertion of a bone-lock mending key into the gripping socket formed in a fractured bone, in accordance with the invention;

FIG. 18 is a cross-sectional side diagram of a mending key installed in a fractured bone, in accordance with the invention.

DETAILED DESCRIPTION OF THE INVENTION

As stated above, this invention involves various techniques for repairing bone fractures, where a "bone-lock" mending key is submerged into the bone to avoid detection of the key through the skin. The invention is especially beneficial for stabilization of small bones, such as the tibia, fibula, radius, ulna, and other small bones. The preferred embodiments and examples shown throughout this description should be considers as exemplars, rather than limitations on the present invention.

Mending Key

Figure 1:
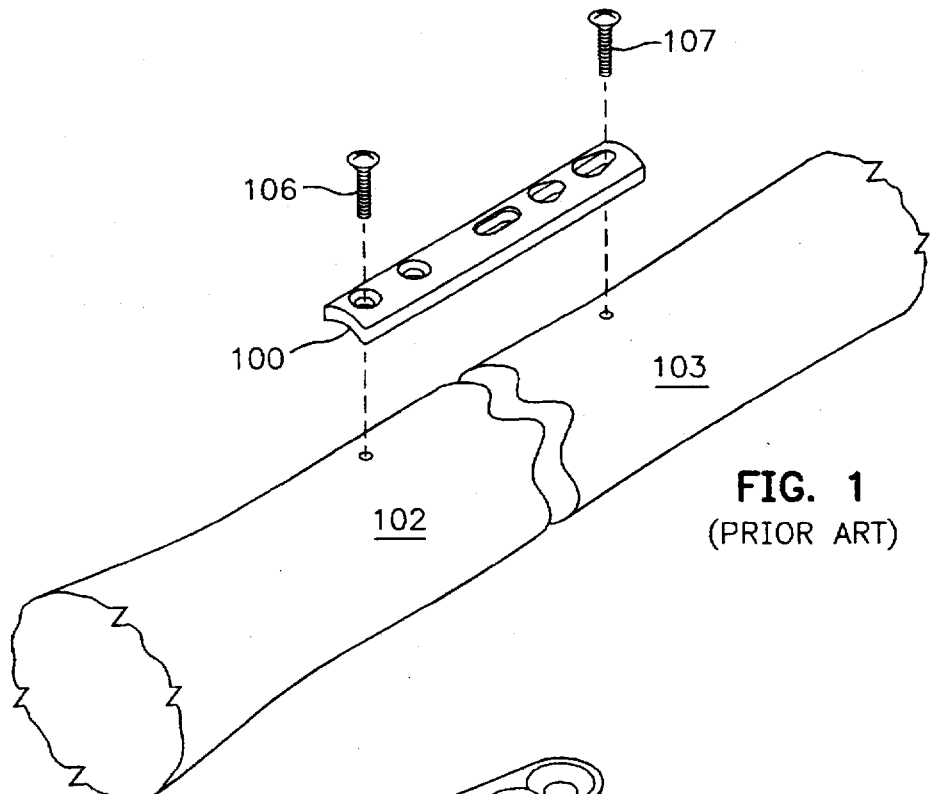
FIG. 1 is an isometric diagram illustrating the installation of a known overlay plate to repair bone fragments.
Figure 2:
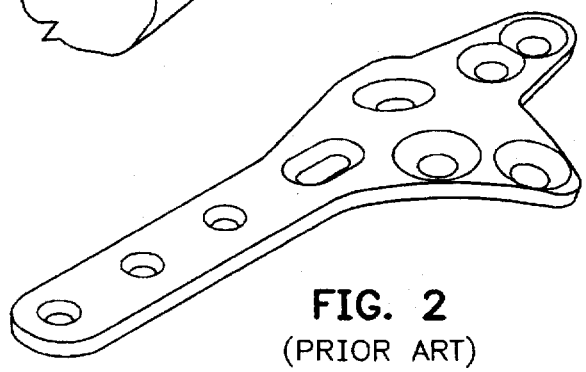
FIG. 2 is an isometric diagram illustrating another known embodiment of overlay plate.
Figure 3:
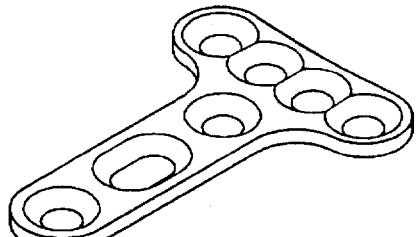
FIG. 3 is an isometric diagram illustrating another known embodiment of overlay plate.
Figure 4:
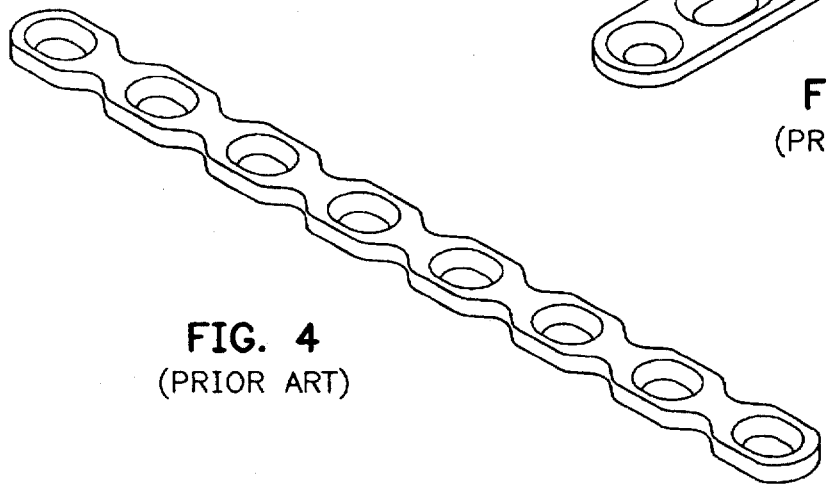
FIG. 4 is an isometric diagram illustrating another known embodiment of overlay plate.
Figure 5:
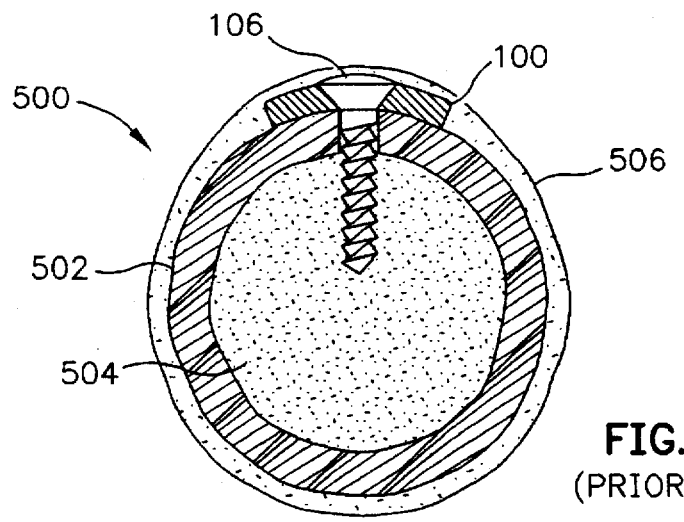
FIG. 5 is a side cross-sectional diagram illustrating a known overlay plate installed in a small bone.
Figure 6:
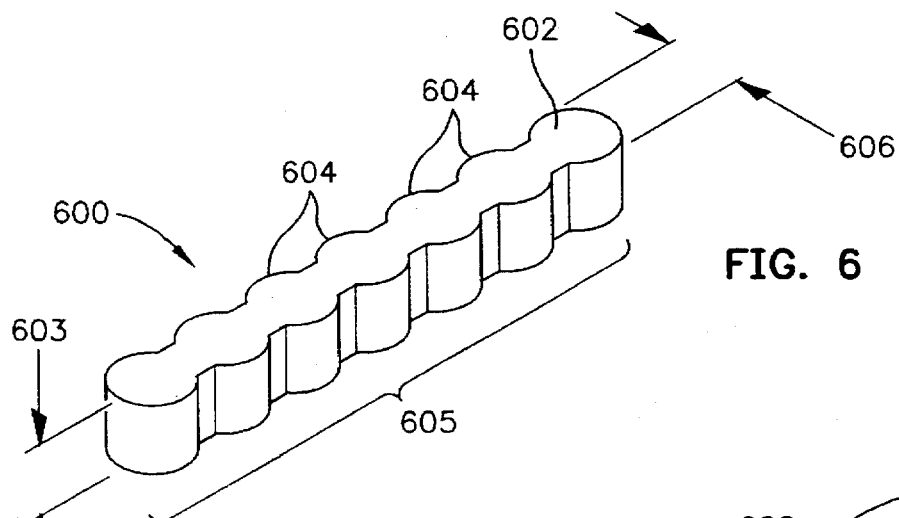
FIG. 6 is an isometric view of a hard "bone-lock" mending key in accordance with the invention.

Broadly, the "bone-lock" mending key of the invention may be embodied by a hard or a soft member, as described in greater detail below. The hard mending key comprises a rigid, pre-formed structure that is pressed into a gripping socket defined in the bone, whereas the soft mending key comprises a soft, fluid or putty-like material that is poured, scooped, or injected into the gripping socket and subsequently hardens in place. FIG. 6 illustrates a mending key 600 in accordance with the invention, which may embody a hard mending key or a soft mending key after hardening. The mending key 600 comprises a unitary member having certain distinctive features designed to engage corresponding features of a receptacle defined in a fractured bone. In a preferred embodiment, the mending key 600 comprises an elongated member 602 or "spar" with multiple gripping protrusions 604 formed thereon. In the preferred embodiment, the gripping protrusions 602 comprise semi-cylindrical rounded bulges, as illustrated. However, this invention also contemplates gripping protrusions 602 that comprise ridges, flanges, knobs, branches, or other suitable protuberances. Although the gripping protrusions are pre-formed in the case of the hard mending key, with the soft mending key these protrusions are created by the hardening of the soft mending key against complimentary shaped surfaces of the gripping socket.

The key 600 may be formed from a bio-absorbable material that is sturdy, durable, lightweight, and pharmacologically non-toxic. As an alternative to bio-absorbable material, the mending key 600 may be formed from Titanium or another appropriate material. The exemplary mending key 600 has a thickness 603 of about 5 mm, a length 605 of about 5–10 cm, and a width 606 of about 7 mm. These dimensions may be varied as needed to suit the size and type of bone being repaired.

Function of Mending Key

Generally, the mending key 600 holds two bone segments together at a fracture site without requiring any bulky material overlying the bone. In the case of small bones this function is referred to as "small bone stabilization."

Figure 7:
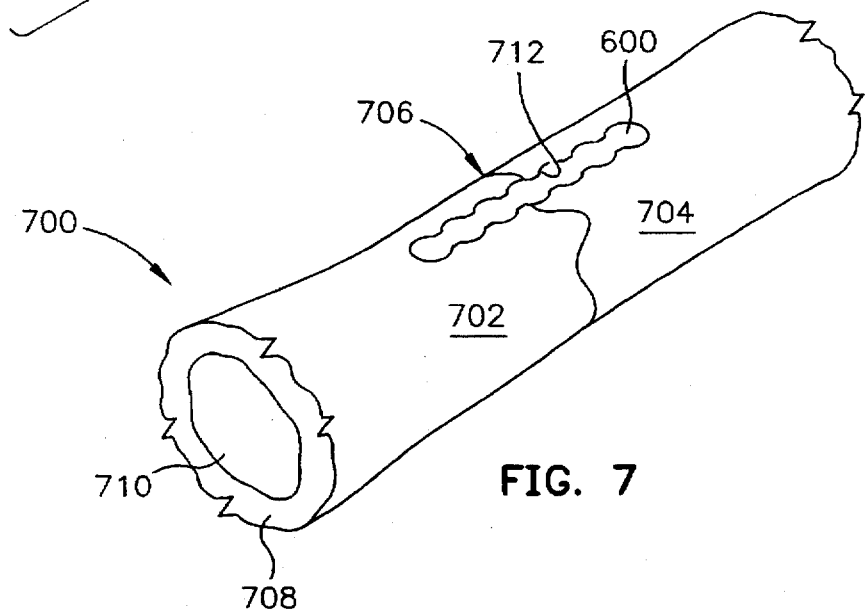
FIG. 7 is a partial cutaway isometric diagram illustrating a mending key of the invention installed in a bone.

As shown in FIG. 7, the bone 700 under repair includes first 702 and second 704 segments, formerly joined at a fracture site 706 (the "fracture"). The bone 700 includes a dense cortical layer 708 and a relatively softer cancellous region 710.

After installation, the mending key 600 snugly resides in a continuous gripping socket 712 that spans the first segment 702, the fracture 706, and the second segment 704. The gripping protrusions 604 of the mending key 600 engage corresponding gripping features of the gripping socket 712, the gripping features being shaped to complementarily mate with the gripping protrusions 604.

Installation of Mending Key

A. Positioning The Bone Segments

Figure 8:
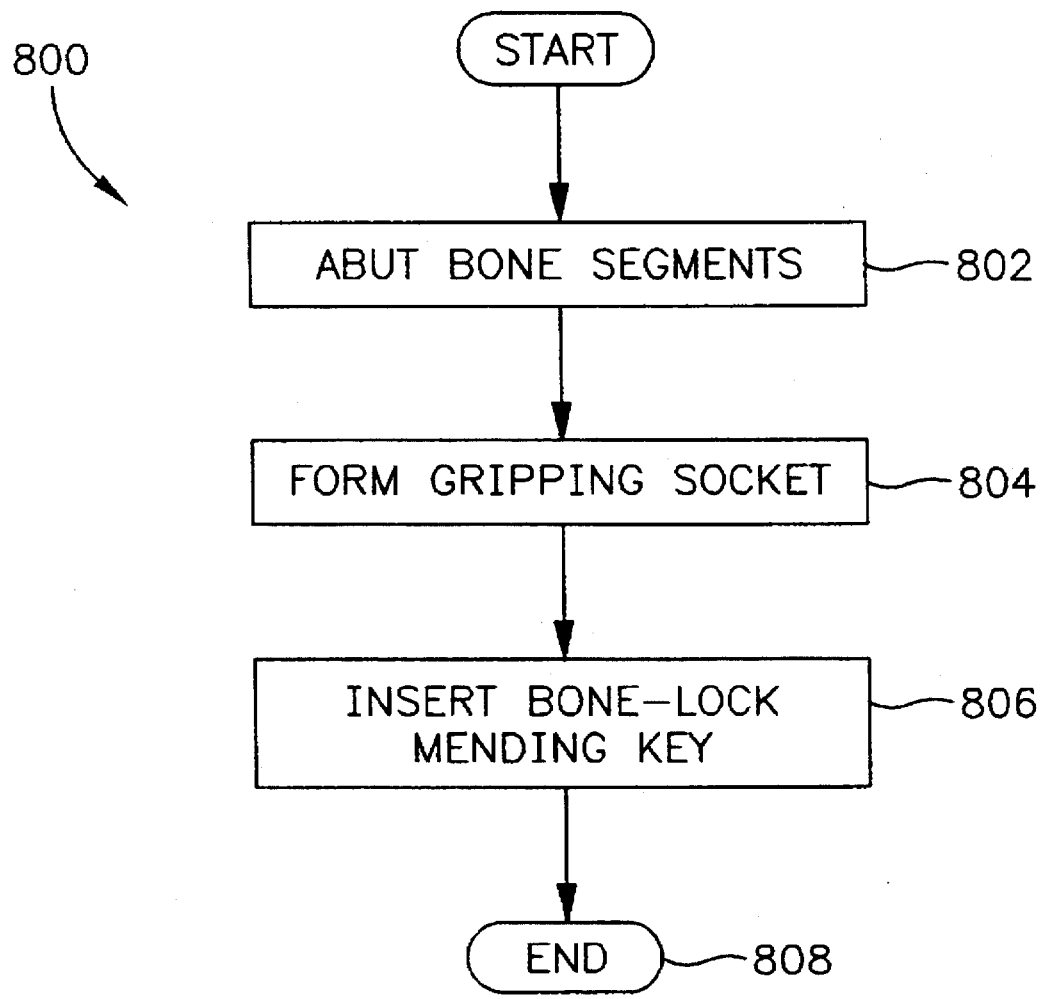
FIG. 8 is a flowchart illustrating an exemplary sequence of method steps in accordance with the invention.

FIG. 8 illustrates an exemplary sequence 800 for installing the mending key 600. The sequence 800 begins in task 802, where the bone segments 702, 704 are abutted, as shown in FIGS. 9–10. The bone segments 702, 704 may have complementary surfaces that mate at a fracture site 706, as illustrated. Thus, if possible, the segments 702, 704 are preferably pieced together at the fracture site 706 to replicate the bone 700 prior to the fracture.

B. Forming The Gripping Socket

Next, the gripping socket 712 is formed in task 804. The gripping socket 712 is made up of corresponding gripping channels (not shown) in the first and second bone segments 702/704. Although each gripping channel may be formed separately, they are preferably created together while the bone segments 702/704 are abutted to form a unitary piece, largely as the bone 700 existed before the fracture occurred.

In the preferred embodiment, the site of the gripping socket 712 is first marked using a template 1100 (FIG. 11). The template comprises a marking overlay 1102, which may be attached to a handle 1104. As illustrated, the overlay 1102 may also include multiple teeth 1106 to keep the overlay 1102 in position with respect to the bone 700. The illustrated overlay 1102 defines a gripping socket pattern using a linear sequence of multiple adjacent holes 1108.

To use the template 1100, the overlay 1102 is placed against the bone 700 such that the line of holes 1108 spans the fracture site 706, in a direction largely coincident with the longitudinal axis of the bone 700. When the overlay 1102 is placed against the bone, the teeth 1106 help keep the overlay 1102 in position.

Figure 12:
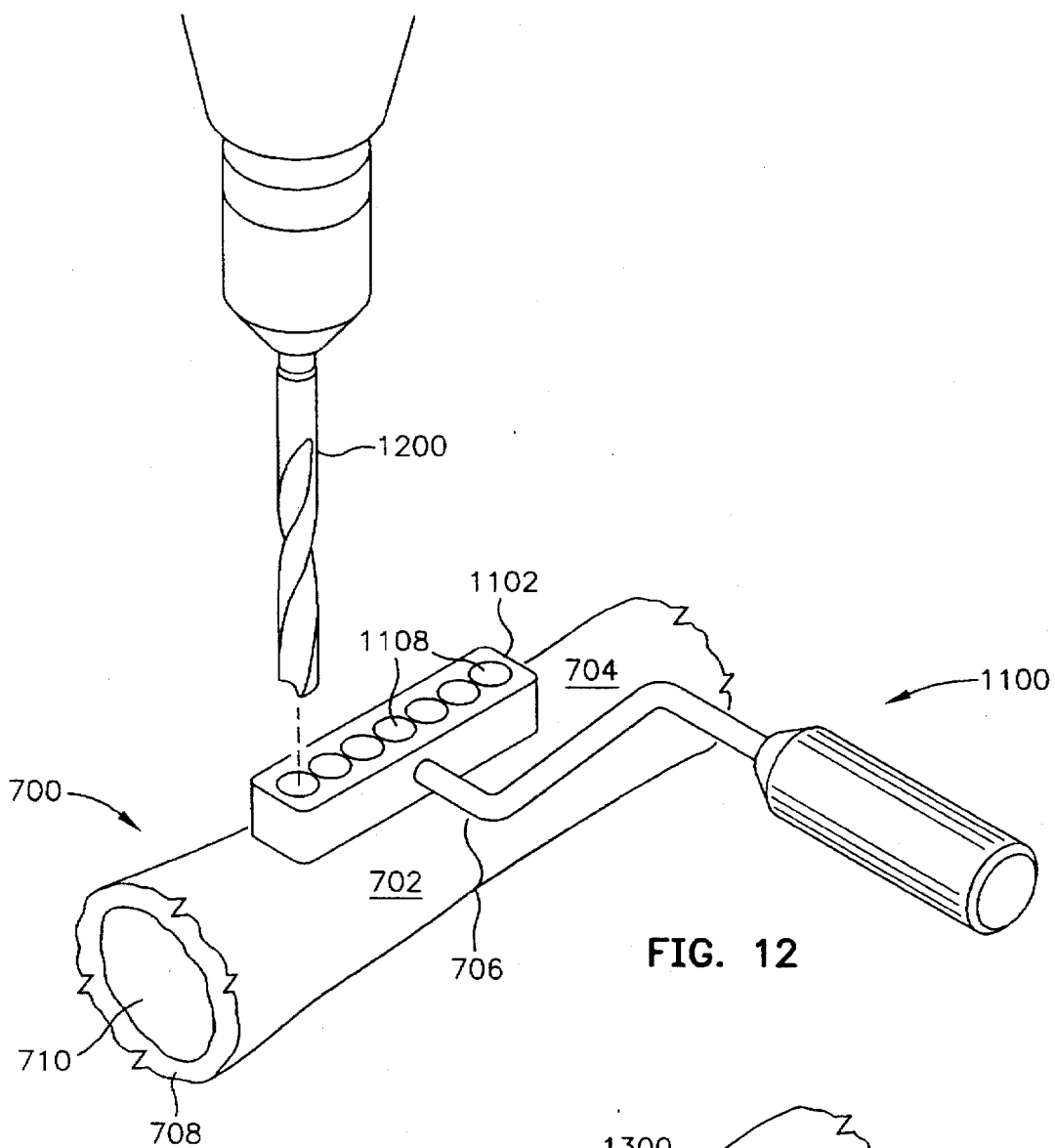
FIG. 12 is an isometric diagram illustrating a drilling step during formation of the gripping socket of the invention.

Next, holes 1300 (FIG. 13) are drilled in the bone 700 using a drill bit 1200 (FIG. 12) having approximately the same diameter as the template holes 1108. Specifically, as the template 1100 rests on the bone 700, each template hole 1108 is used as a guide for the drill bit 1200 to drill a corresponding hole 1300 in the bone 700. In the case of a hard mending key, the diameter of the holes 1300 is preferably chosen to be slightly smaller (e.g. 1 mm) than the diameter of the cylindrical gripping protrusions 604 to ensure a snug fit between the socket and mending key, as discussed below; likewise, the holes 1300 are preferably drilled to a depth corresponding to the thickness 602 of the mending key 600.

Having created the holes 1300, the gripping socket is completed by removing the bone material remaining between the holes 1300. This may be achieved, for example, by sawing across the holes 1300 using a circular surgical saw 1400 (FIG. 14). Continuing to abut the bone segments 702/704 during sawing is preferable, since it encourages formation of a continuous, straight socket 712. The saw blade's width preferably resembles the width of the elongated member 602.

After sawing is completed, the gripping socket 712 is complete, as shown in FIG. 15. The gripping socket 712 includes a longitudinal passage 1502 with multiple gripping features 1504 extending outward from the passage 1502. In the illustrated example, the gripping socket 712 has a "caterpillar" pattern, where multiple adjacent circular holes are positioned in a line with a central channel extending through the circles. Although the gripping features 1504 have been exemplified by rounded recesses in the socket 712, other arrangements (not shown) are possible, such as fingers, branches, and other apertures that extend outward from the longitudinal passage 1502 to form complimentarily sized ridges, flanges, and other protuberances of bone.

Figure 13:
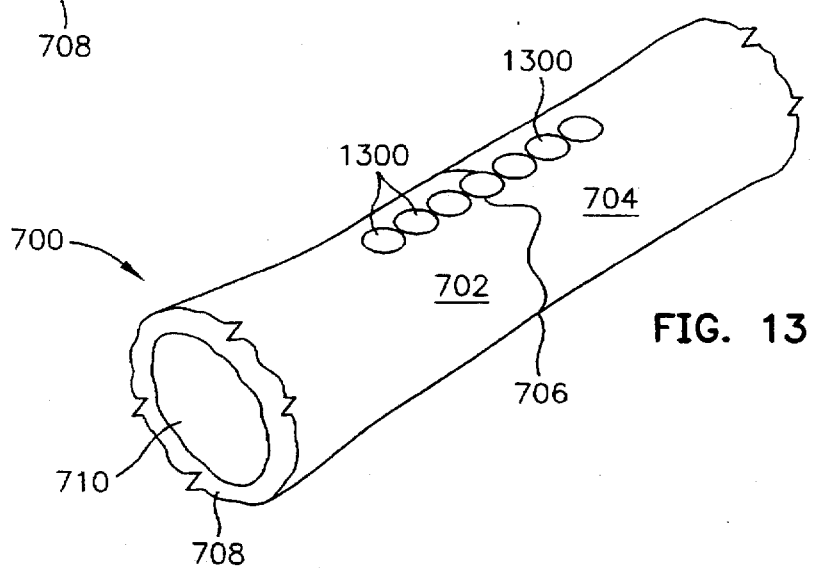
FIG. 13 is an isometric diagram illustrating preliminary holes formed during creation of the gripping socket of the invention.

In the embodiment created according to FIGS. 13–14, the socket 712 is positioned to approximately bisect the bone 700. This embodiment provides an even number (e.g. three, as illustrated) of cylindrical protrusions 604 in each bone segment 702/704, with a middle protrusion residing at the fracture site 706. This arrangement may be adjusted, however, to suit the application. For example, the gripping socket may extend into one bone segment more than the other if the fracture resides near a joint, blocking further extension of the gripping socket.

C. Installing The Mending Key

Figure 17:
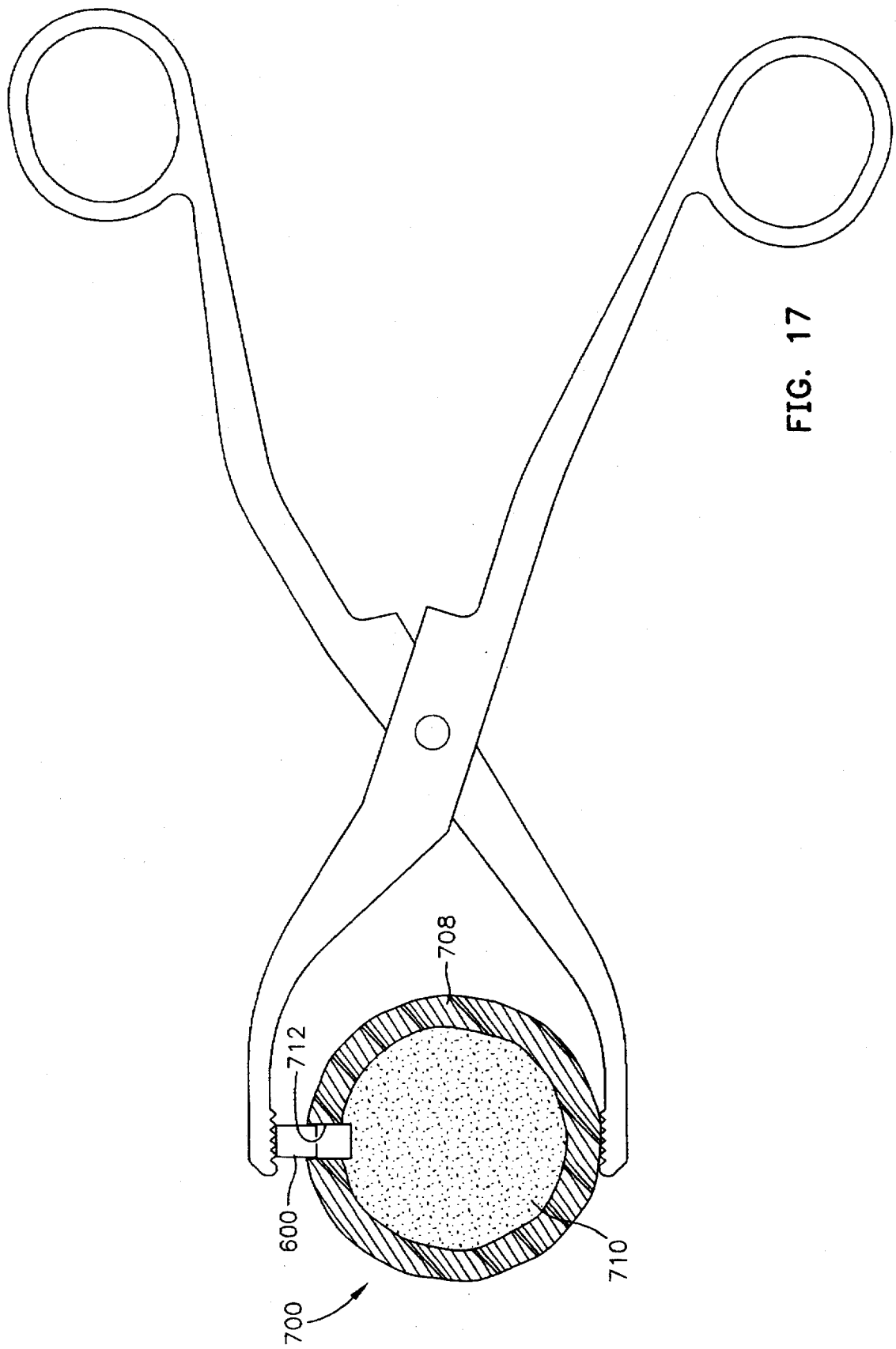
FIG. 17 a side cross-sectional diagram showing the use of surgical pliers to install a hard bone-lock mending key by pressing it into the gripping socket, in accordance with the invention.

After defining the gripping socket in task 804, the bone-lock mending key 600 is installed into the bone 700 in task 806. In the case of a hard mending key, the mending key 600 is first aligned with the gripping socket 712, as shown in FIG. 16. Then, the mending key 600 is slidably inserted into the socket 712. In particular, the bone segments 702/704 are held together at the fracture site 706 while the mending key 600 is pressed into the socket 712. Pressing the mending key 600 into the socket 712 firmly wedges the key 600 into the gripping socket 712, since the key 600 is slightly larger than the gripping socket 712. In this respect, it may be helpful to install the mending key 600 with pliers, vice, or another type of leverage, as shown in FIG. 17.

In contrast to the preceding description, if a soft mending key is used, the soft mending key material is poured, scooped, injected or otherwise transferred into the gripping socket 712. The soft mending key material is preferably forced into the gripping socket 712 with sufficient force to extrude gripping protrusions 604 with complimentary shapes to the gripping socket 712, as shown in FIG. 6. Then, the soft mending key (including the gripping protrusions of FIG. 6) is permitted to harden while the bone segments 702/704 are secured in place by a cast, splint, or another suitable immobilizing device.

D. Completing the Sequence

After installing the key 600 in task 806, the sequence 800 ends in task 808. Although not shown, standard techniques are performed to treat the wound, suture the skin together about the bone 700, etc.

FIGS. 7 and 18 depict the key 600 as installed. The mending key 600 resides in the cortical bone 708, and possibly the cancellous layer 710, depending upon the thickness of the key 600 and the size of the cortical bone 708. Importantly, the key 600 lies flush with the cortical bone's outer surface, and cannot be detected through the overlying dermis ("skin") 1800.

As explained above, the key 600 holds the bone segments 702/704 together because the gripping protrusions 604 engage the socket's complementary gripping features 1504. In the case of a hard bone-lock mending key, the tight fit between the mending key 600 and the socket 712 further prevents the key 600 from exiting the socket 712.

Also, healing and recovery of the patient is aided by the bio-absorbable nature of the mending key. In particular, the mending key is assimilated into the repaired bone as a result of the body's natural healing process.

Other Embodiments

While there have been shown what are presently considered to be preferred embodiments of the invention, it will be apparent to those skilled in the art that various changes and modifications can be made herein without departing from the scope of the invention as defined by the appended claims.

For example, the holes 1300 may be positioned to slightly intersect each other, thereby forming a single contiguous hole without requiring any sawing of bone between the holes. And, although the holes 1300 have been shown in linear alignment, this invention also contemplates other engagements, such as an arcuate pattern, an "s" curve, etc. Further, the holes 1300 may include a variety of different diameters. And, although circular holes 1300 were described as a preferred embodiment, ordinarily skilled artisans with the benefit of this disclosure will recognize that a wide variety of other shapes may be used.

What is claimed is:

1. A method for re-attaching first and second parts of a bone, said parts having mating surfaces defined by a fracture, the method comprising the steps of:
   abutting the mating surfaces; and
   while continuing to abut the mating surfaces, performing steps comprising:
      defining a line of multiple holes from the first mating part to the second mating part via the fracture;
      excavating paths between the holes to form a gripping socket defined by the holes and the paths therebetween;
      aligning a rigid mending key with the gripping socket, said mending key having a shape substantially similar to the gripping socket but sufficiently larger in size to provide a snug fit upon insertion of the mending key into the gripping socket; and pressing the mending key a predetermined distance into the gripping socket, the mending key engaging the gripping socket to hold the bone parts together.

2. The method of claim 1, the line being a substantially straight line.

3. The method of claim 1, the first and second bone parts having an outer cortical layer, the predetermined distance being selected such that the mending key when passed into the gripping socket is substantially flush with the outer cortical layer.

4. The method of claim 1, the excavating step comprising a step of sawing paths between the holes.

5. The method of claim 1, the mending key comprising an elongated spar having multiple gripping protrusions extending therefrom.

6. The method of claim 1, the key being made of Titanium.

7. The method of claim 1, the key being made of a bio-absorbable material.

8. A method for repairing a bone fracture that defines first and second segments of bone, a method comprising the steps of:

defining respective first and second gripping channels in the first and second segments, the gripping channels being positioned such that the first and second gripping channels form a continuous gripping socket when the first and second segments are abutted at the fracture, the gripping socket including multiple gripping features having one or more predetermined shapes;

abutting the first and second segments at the fracture;

continuing to abut the first and second segments at the fracture while performing steps comprising:

placing a shapeable mending material into the gripping socket; and hardening the mending material in place to form a rigid mending key having one or more gripping protrusions shaped to substantially compliment the gripping features, the gripping protrusions engaging the gripping features to prevent the bone segments from moving away from each other.

9. The method of claim 8, the mending material being bio-absorbable.

10. The method of claim 8, the step of defining first and second gripping channels comprising the steps of:

drilling a sequence of holes in the first and second bone segments; and excavating a channel interconnecting the drilled holes.

11. The method of claim 10, the step of defining first and second gripping channels further comprising the steps of, before the drilling step, using a template to mark hole drilling positions in the first and second bone segments.

12. The method of claim 11, the step of using the template comprising the steps of:

placing the template over the first and second bone segments, said template having multiple template holes defined therein;

inserting a drill bit into predetermined ones of the template holes and drilling corresponding holes in the first and second bone segments; and removing the template from the first and second bone segments.

13. The method of claim 8, the step of defining first and second gripping channels being performed while holding the first and second segments together at the fracture.

14. The method of claim 8, the bone having an outer cortical layer surrounding an inner cancellous region, the first and second gripping channels extending through the cortical layer and into the cancellous region.

15. The method of claim 8, the bone having an outer cortical layer surrounding an inner cancellous region, the first and second gripping channels extending into the cortical layer without extending into the cancellous region.

16. A method for joining first and second bone members, said bone members having been previously joined at a fracture site to form a unitary piece of bone, said method comprising the steps of:

uniting the first and second bone members at the fracture site;

holding the fractured bone members together at the fracture site while performing steps comprising:

defining a gripping socket from the first bone member to the second bone member across a fracture site, the gripping socket having multiple gripping features;

placing a shapeable mending material into the gripping socket; and hardening the mending material in place to form a rigid mending key having gripping protrusions complimentarily engaging the gripping socket.

17. A method for re-attaching first and second parts of a bone, said parts having mating surfaces defined by a fracture, the method comprising the steps of:

abutting the mating surfaces; and while continuing to abut the mating surfaces, performing steps comprising:

defining a line of multiple holes from the first mating part to the second mating part via the fracture;

excavating paths between the holes to form a gripping socket defined by the holes and the paths therebetween;

placing a mending material into the gripping socket;

hardening the mending material in place to form a rigid mending key having a shape substantially similar to the gripping socket; and the hardened mending key engaging the gripping socket to hold the bone parts together.

18. The method of claim 17, the line being a substantially straight line.

19. The method of claim 17, the first and second bone parts having an outer cortical layer, the hardened mending key being substantially flush with the outer cortical layer.

20. The method of claim 17, the excavating step comprising a step of sawing paths between the holes.

21. Method of claim 17, the mending material being bio-absorbable.

22. The method of claim 17, the mending material being a fluid.

23. The method of claim 17, the mending material being a solid.

24. The method of claim 23, the mending material being a plastic substance.

25. The method of claim 17, the step of placing the mending material into the gripping socket being performed by scooping the mending material into the gripping socket.

26. The method of claim 17, the step of placing the mending material into the gripping socket being performed by injecting the mending material into the gripping socket.

27. The method of claim 17, the step of placing the mending material into the gripping socket being performed by extruding the mending material into the gripping socket.

28. The method of claim 17, the step of placing the mending material into the gripping socket being performed by pouring the mending material into the gripping socket.

* * * * *